US006999847B2

(12) United States Patent
Barry et al.

(10) Patent No.: US 6,999,847 B2
(45) Date of Patent: Feb. 14, 2006

(54) SPECIMEN CARRIER TRANSFER APPARATUS FOR A CONVEYOR TRACK

(75) Inventors: Douglas Barry, Lincoln, NE (US); Thomas L. Bybee, Omaha, NE (US); Adrian Chan, Richmond Hill (CA); John Fuller, Omaha, NE (US); Ray Puseman, Bellevue, NE (US); Greg Rothman, Omaha, NE (US); Don R. Simms, Council Bluffs, IA (US); Michael Turner, Bellevue, NE (US); Jay Woods, Omaha, NE (US); Inna M. Zevakina, Omaha, NE (US)

(73) Assignee: UNeLab LLC, Omaha, NE (US)

( * ) Notice: Subject to any disclaimer, the term of this patent is extended or adjusted under 35 U.S.C. 154(b) by 7 days.

(21) Appl. No.: 10/626,466

(22) Filed: Jul. 24, 2003
(Under 37 CFR 1.47)

(65) Prior Publication Data
US 2004/0163931 A1 Aug. 26, 2004

Related U.S. Application Data

(60) Provisional application No. 60/398,893, filed on Jul. 26, 2002.

(51) Int. Cl.
*G06F 7/00* (2006.01)
(52) U.S. Cl. .............. 700/213; 198/468.11; 198/468.2; 198/346.1
(58) Field of Classification Search .......... 198/468.11, 198/468.01, 468.2, 468.9, 459.5, 346.2, 456, 198/458, 597, 465.1, 570, 345.3, 346.1; 700/213
See application file for complete search history.

(56) References Cited

U.S. PATENT DOCUMENTS

| | | | | | |
|---|---|---|---|---|---|
| 1,726,657 | A | * | 9/1929 | Ekvall | 198/468.2 |
| 2,451,104 | A | * | 10/1948 | Lowe | 198/442 |
| 3,160,259 | A | * | 12/1964 | Dalton | 198/432 |
| 4,325,476 | A | * | 4/1982 | Eddy | 198/448 |
| 4,741,429 | A | * | 5/1988 | Hattori et al. | 198/456 |
| 4,809,839 | A | * | 3/1989 | Elliott | 198/766 |
| 5,228,551 | A | * | 7/1993 | Kluttermann et al. | 198/468.11 |
| 6,328,153 | B1 | * | 12/2001 | Manghi et al. | 198/736 |
| 6,435,336 | B1 | * | 8/2002 | Knodler | 198/474.1 |

* cited by examiner

Primary Examiner—Richard Ridley

(57) ABSTRACT

A transfer apparatus includes a shuttle depending from an overhead support with a pair of arms for receiving and shifting a specimen carrier from one conveyor to a second conveyor of a dual-conveyor track. The shuttle is operable to retain a specimen carrier along either the first or second conveyor and to release a specimen carrier along either the first or second conveyor. Sensors are located to detect the presence of a specimen carrier at each of the retention locations, and to confirm the release of a specimen carrier from the shuttle along each of the conveyors. A drive motor for moving the shuttle between the retention and release positions is electrically connected to a command module with a processor, for receiving instructions as to the position of the shuttle. The sensors are also connected to the processor to transmit detection data to the processor. A queue is positioned upstream of the shuttle and is electrically connected to the processor. The queue includes retractable shafts, sensors and scanners for selectively retaining, detecting and scanning identification data from a specimen carrier on either conveyor upstream of the shuttle, and transmitting the information to the processor.

13 Claims, 8 Drawing Sheets

SPECIMEN CARRIER TRANSFER APPARATUS FOR A CONVEYOR TRACK

CROSS-REFERENCES TO RELATED APPLICATIONS

This application claims the benefit of U.S. Provisional Application Ser. No. 60/398,893, filed Jul. 26, 2002.

STATEMENT AS TO RIGHTS TO INVENTIONS MADE UNDER FEDERALLY SPONSORED RESEARCH AND DEVELOPMENT (Not applicable)

BACKGROUND OF THE INVENTION (1) Field of the Invention

The present invention relates generally to track utilized in an automated clinical laboratory conveyor system, and more particularly to an improved specimen carrier transfer apparatus for transferring specimen carriers from one track loop to another in a dual track system.

(2) Background Information

Clinical laboratory testing has changed and improved remarkably over the past 80 years. Initially, tests or assays were performed manually and generally utilized large quantities of serum, blood or other materials and/or body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of physical specimen required to perform a particular test.

Instruments have been developed to increase the efficiency of testing procedures by reducing turnaround time and decreasing the volumes necessary to perform various assays. Robotic engineering has evolved to such a degree that various types of robots have been applied in the clinical laboratory setting.

The main focus of prior art laboratory automation relied on the implementation of conveyor systems to connect areas of a clinical laboratory. Known conveyor systems in the laboratory setting utilize separate conveyor segments to move specimens from a processing station to a specific laboratory work station. In order to obtain cost savings, one typical scenario called for specimens to be sorted manually and grouped together in a carrier rack to be conveyed to a specific location. In this way, a carrier would move a group of 5–20 specimens from the processing location to the specific work station for the performance of a single test on each of the specimens within the carrier rack.

With the development of new and improved automatic conveyor systems for laboratories and other environments, it is possible to select, track, and convey individual specimens throughout a laboratory for a variety of different testing, while maintaining a priority system for certain types of testing or special urgent requests for a time-specific response. These new automated conveyor systems are of various types and design, but the inventors herein have found that a dual conveyor system, using a pair of parallel conveyor tracks circulating throughout a laboratory, provides the greatest flexibility and versatility. The integration of various track devices with software directing the operation of the conveyor system and the various automated testing stations, has improved both the speed and capability of automated conveyor systems in recent years.

Track devices form the physical interface between the specimen samples in carriers being directed throughout the system, while the Laboratory Automation System (LAS) database provides direction for the system through its command and control features. The LAS and the various track devices work in combination to direct, manage and track all specimens throughout the system.

The dual-lane conveyors used in the present invention utilize table top chain to transport specimen carriers about a closed loop among various stations. Typically, the inside lane of the dual lane conveyor acts as a highway to rapidly transport specimens to their proper destination. The outside lane accepts specimens diverted to it from the inside lane, and queues them for processing at one of the automation system modules or laboratory instruments. The continuous loop dual lane design means that specimens will quickly circulate back to any module or instrument on the system without operator intervention. Rules based processing guidelines determine all specimen actions, including routing changes for additional testing or modified processing.

In order to effectively manage, track and route specimens throughout a clinical laboratory, it is necessary to maintain constant "awareness" of the location of every specimen throughout the system, and be able to direct each specimen to the appropriate location at the most appropriate time for storage, testing or other processing. This in turn is accomplished, in part, by one or more transfer apparatus for selectively shifting a specimen carrier between the inside and outside lanes of the dual lane conveyor.

BRIEF SUMMARY OF THE INVENTION

It is therefore a general object of the present invention to provide an improved transfer apparatus for selectively moving specimen carriers between the lanes of a dual lane, closed loop conveyor in an automated conveyor system.

These and other objects will be apparent to those skilled in the art.

The transfer apparatus of the present invention includes a shuttle depending from an overhead support with a pair of arms for receiving and shifting a specimen carrier from one conveyor to a second conveyor of a dual-conveyor track. The shuttle is operable to retain a specimen carrier along either the first or second conveyor and to release a specimen carrier along either the first or second conveyor. Sensors are located to detect the presence of a specimen carrier at each of the retention locations, and to confirm the release of a specimen carrier from the shuttle along each of the conveyors. A drive motor for moving the shuttle between the retention and release positions is electrically connected to a command module with a processor, for receiving instructions as to the position of the shuttle. The sensors are also connected to the processor to transmit detection data to the processor. A queue is positioned upstream of the shuttle and is electrically connected to the processor. The queue includes retractable shafts, sensors and scanners for selectively retaining, detecting and scanning identification data from a specimen carrier on either of the conveyors, upstream of the shuttle, and transmitting the information to the processor.

BRIEF DESCRIPTION OF THE SEVERAL VIEWS OF THE DRAWING

The preferred embodiment of the invention is illustrated in the accompanying drawings, in which similar or corresponding parts are identified with the same reference numeral throughout the several views, and in which.

DETAILED DESCRIPTION OF THE INVENTION

Figure 1:
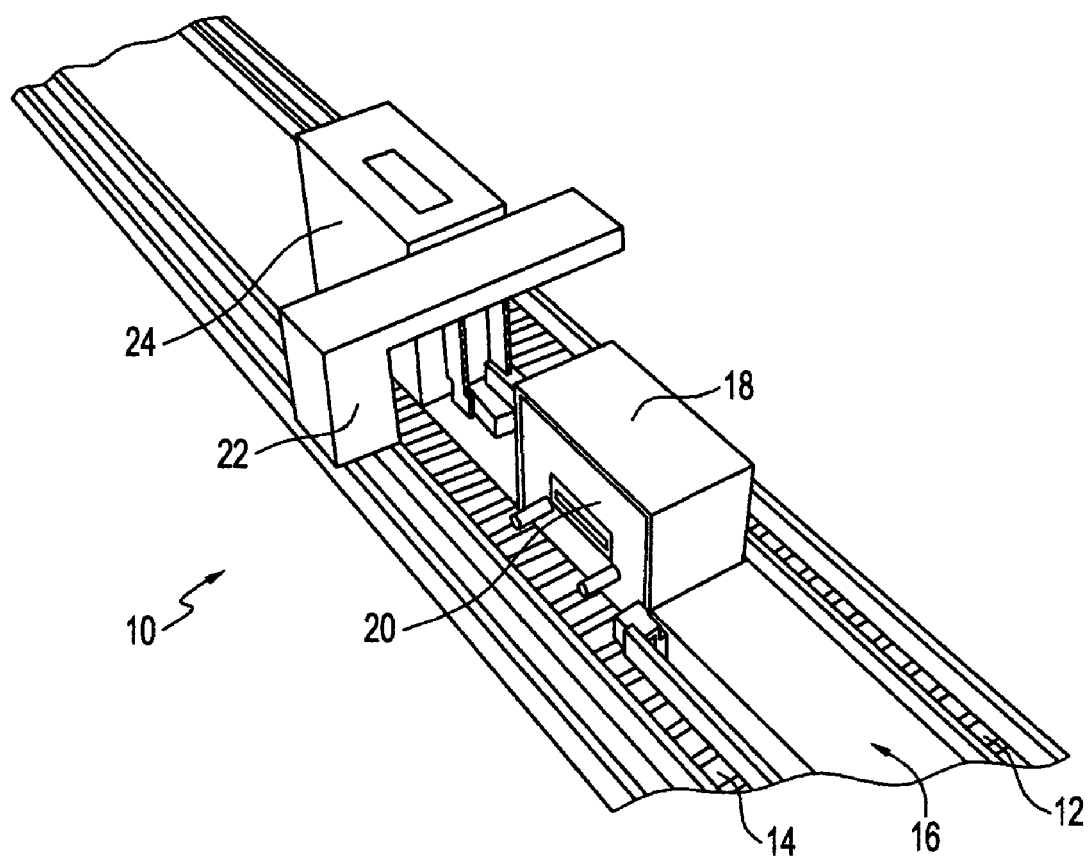
FIG. 1 is a perspective view of a transfer apparatus of the present invention installed along a dual lane conveyor track.

Referring now to the drawings, in which similar or corresponding parts are identified with the same reference numeral, and more particularly to FIG. 1, the transfer apparatus of the present invention is designated generally at 10, and is shown installed between two conveyors 12 and 14 of a dual lane automated conveyor transport track 16, to selectively transfer a specimen carrier 18 between conveyors 12 and 14. Transfer apparatus 10 includes three general components: a queue 20, a lane changer 22 and a command module 24. Queue 20 serves to stop each specimen carrier 18 that travels by the queue, identify the carrier 18 and then release the carrier at a time determined by the command module 24. Lane changer 22 is operated by the command module 24 to receive and shift a specimen carrier 18 from one of conveyors 12 or 14, to the other. The command module 24 serves as the "brain" of the transfer apparatus 10 and interacts with the Laboratory Automation System (LAS) to identify, track and direct specimen carriers 18 through the transfer apparatus 10.

Figure 2:
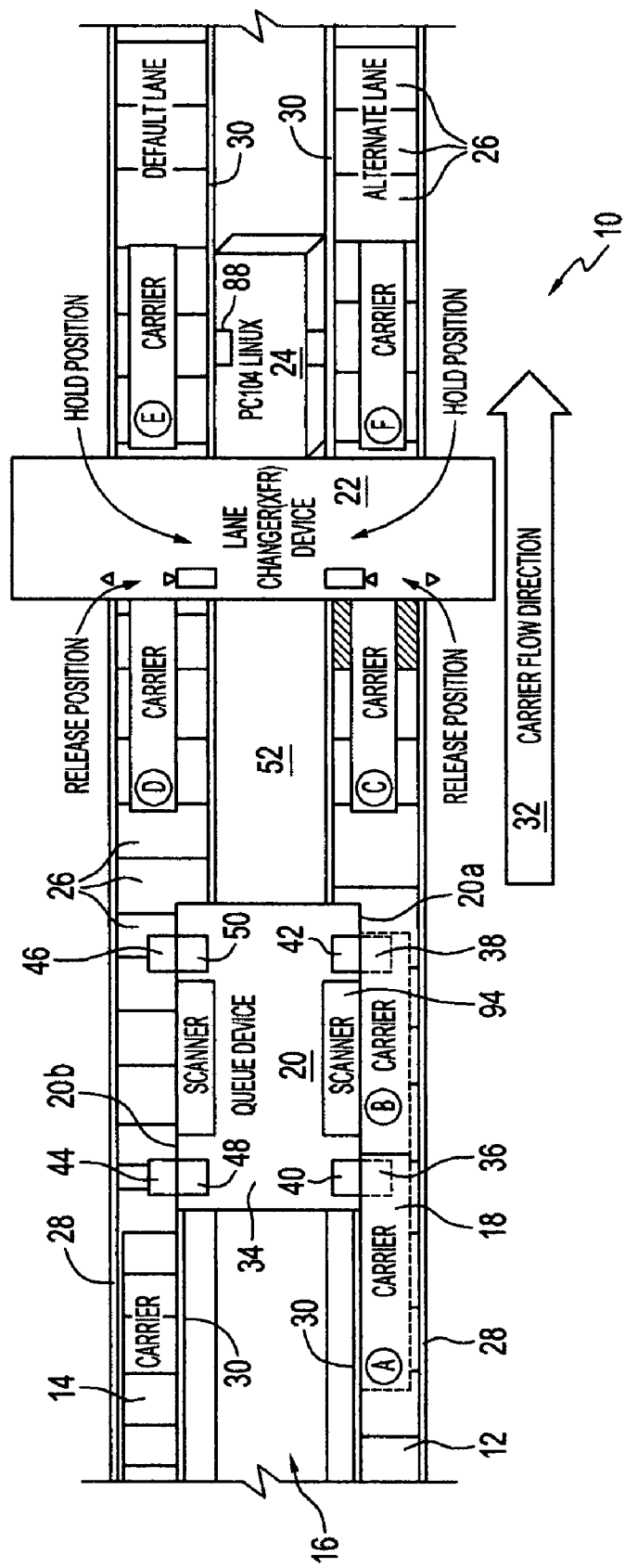
FIG. 2 is a top plan view of the transfer apparatus module, showing various possible positions of a specimen carrier as the transfer apparatus operates.

Referring now to FIG. 2, conveyors 12 and 14 use a table top chain known in the art to transport specimen carriers 18. Each table top chain includes a plurality of plates 26, each having a flat upper surface or "table top" for moving carriers 18. Plates 26 are interconnected by links, which permit plates 26 to pivot about the links within a horizontal plane. The links are engaged by a drive mechanism to pull the chain along track 16 and thereby move carriers 18 supported on the track. The upper surfaces of plates 26 form a flat planar surface identified throughout this specification as a drive plane.

A pair of elongated guide rails 28 and 30 are disposed along the lengths of each conveyor 12 and 14 on opposing sides of plates 26 to guide specimen carriers 18 therebetween. One embodiment of specimen carriers 18 is disclosed throughout this specification, but it should be understood that many other sizes and shapes of carriers for specimens could be utilized with the present invention. Each specimen carrier 18 includes a generally rectangular body with a forward wall and a top surface. A plurality of openings are formed in the top surface and extend into the interior of the body for receiving and supporting a specimen tube, slide, or other specimen container in an upright position.

Conveyors 12 and 14 operate in the same direction, designated generally by arrow 32, although they may be operated at different speeds. Queue 20 includes a housing 34 positioned between conveyors 12 and 14 and located upstream of lane changer 22. A pair of forward and rearward retractable shafts 36 and 38 extend transversely outwardly from a first side 20a of queue 20, and project over conveyor 12 to restrain a specimen carrier 18 from passing by shaft 36 or 38. Forward and rearward sensors 40 and 42 are positioned adjacent each shaft 36 and 38, respectively, to detect the presence of a specimen carrier 18 at the associated shaft.

A second pair of forward and rearward retractable shafts 44 and 46 extend transversely outwardly from the opposing second side 20b of queue 20, and project over conveyor 14 to restrain a specimen carrier 18 from passing by shaft 44 or 46. Forward and rearward sensors 48 and 50 are positioned adjacent each shaft 44 and 46, respectively, to detect the presence of a specimen carrier 18 at the associated shaft.

In the preferred embodiment of the invention, forward shafts 36 and 44 are the projecting ends of a single shaft. In this way, only one carrier 18 is permitted to continue downstream at a time, since the retraction of one end of the shaft would cause the other end to project farther over the opposing track. Similarly, rearward shafts 38 and 46 are preferably the projecting ends of a second single shaft. Again, only one carrier is permitted to advance downstream from queue 20 along the conveyors 12 and 14.

The inward guide rails 30 of conveyors 12 and 14 are removed from between the downstream end of queue 20 and lane changer 22, and a platform 52 is installed with its top surface coplanar with the drive plane of conveyors 12 and 14. Thus, carriers 18 may be moved off of one conveyor and onto the other by sliding the carrier across platform 52.

Figure 3:
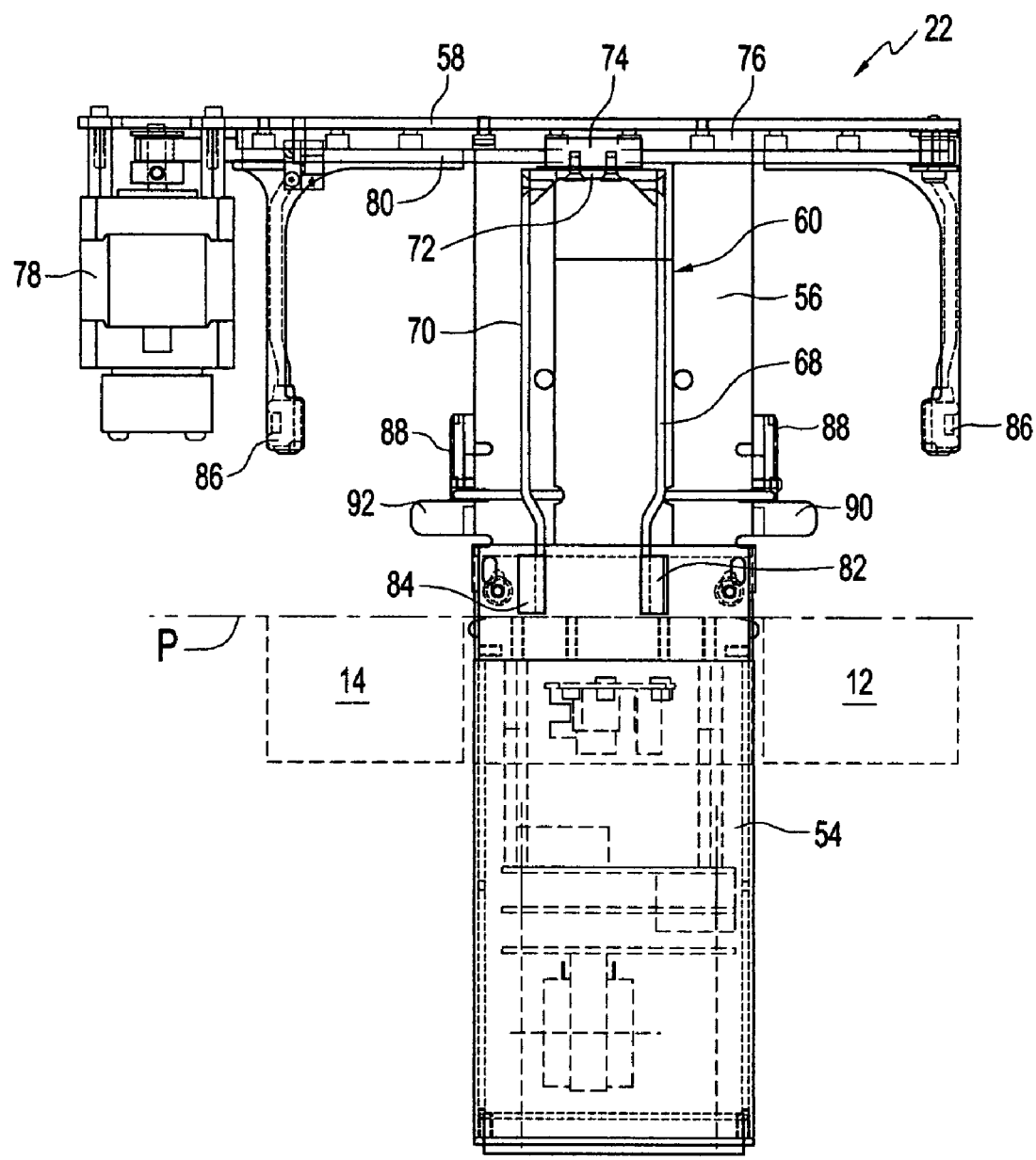
FIG. 3 is a front elevational view of the transfer apparatus.
Figure 4:
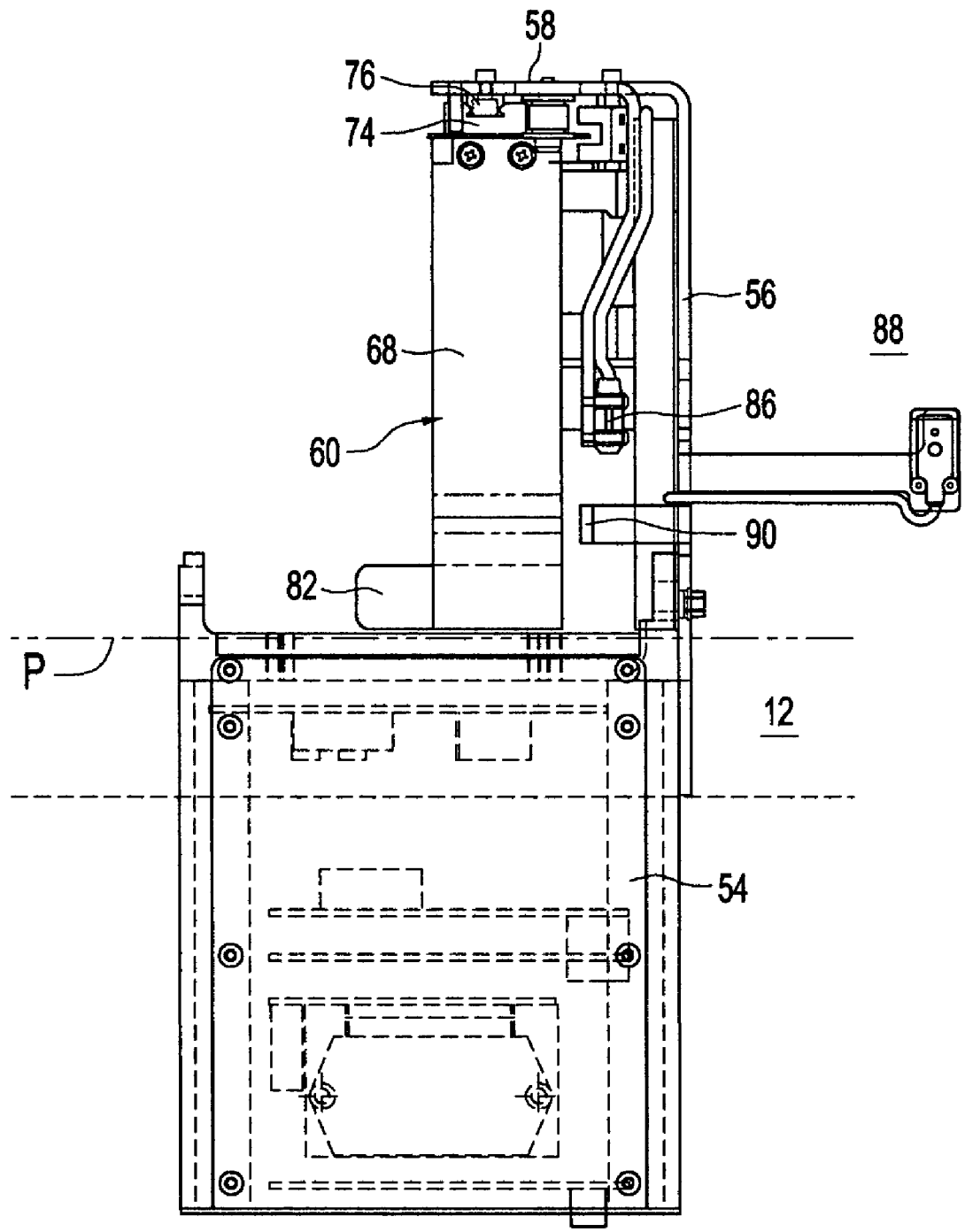
FIG. 4 is a side elevational view of the transfer apparatus.
Figure 5:
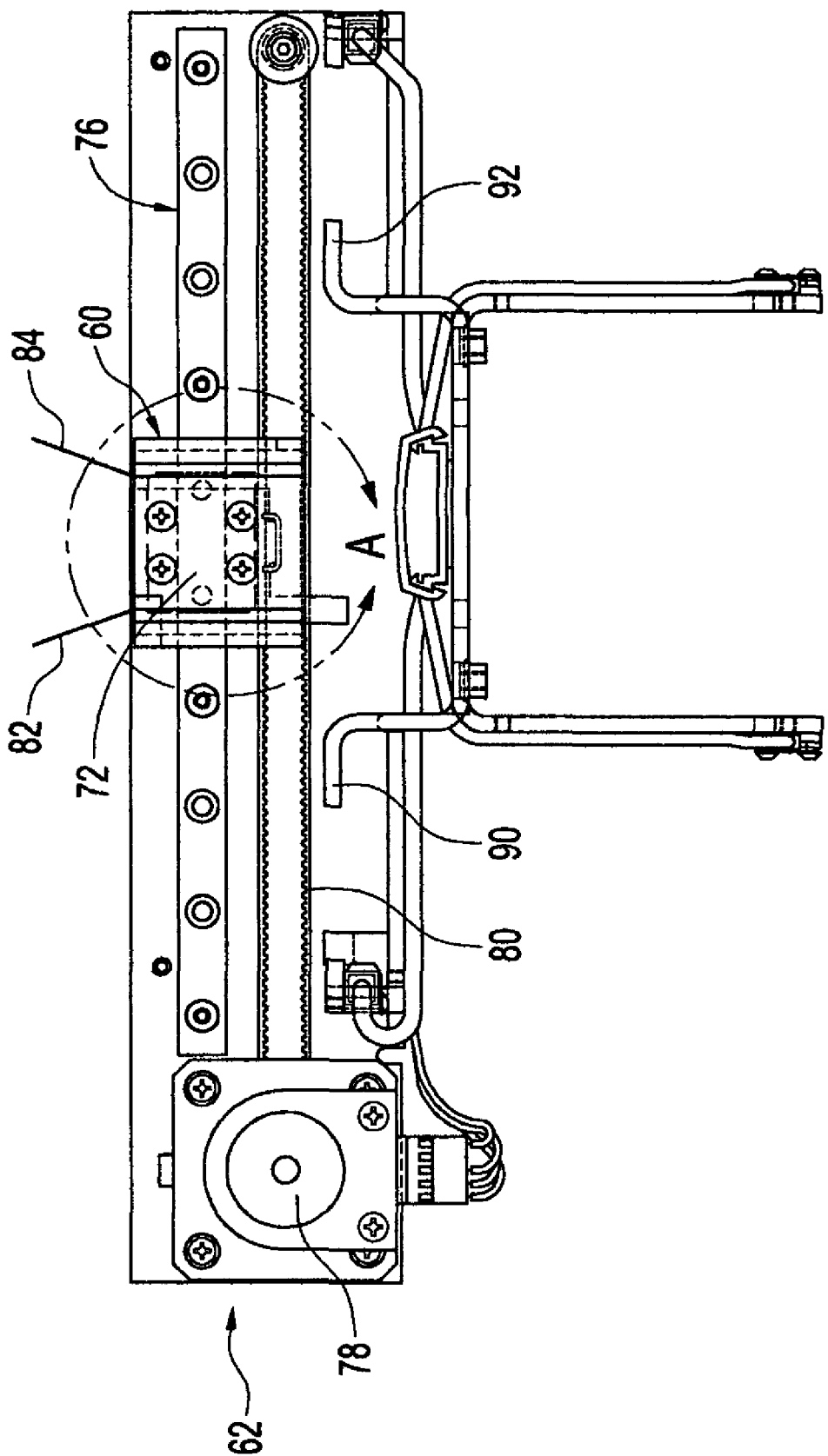
FIG. 5 is a bottom view of the drive assembly of the transfer apparatus.

As shown in FIGS. 3 and 4, lane changer 22 includes a lower housing 54 mounted between conveyors 12 and 14 and depending below the drive plane "P". A rigid upright back 56 is connected at its lower end to housing 54 and projects upwardly between conveyors 12 and 14. A support plate 58 projects forwardly and transversely outwardly from the top of back 56, and serves as the frame for supporting the shuttle 60, the shuttle drive assembly 62 and sensors 64 and 66, all of which are described in more detail hereinbelow.

Shuttle 60 serves to receive a specimen carrier 18 between a pair of arms 68 and 70 and transversely move carrier 18 between conveyors 12 and 14, and includes a base plate 72 connecting the upper ends of arms 68 and 70 to form an inverted U-shaped structure. Base plate 72 is mounted to the bottom of a slide 74 which in turn is slidably connected to a linear rail 76 on the bottom of support plate 58. As shown in FIG. 3, linear rail 76 extends transversely over both conveyors 12 and 14, thereby permitting movement of shuttle 60 over both conveyors. An encoder-monitored DC stepper motor 78 selectively drives a drive belt 80 connected to slide 74 to precisely position shuttle 60 where desired along rail 76.

The lower ends of arms 68 and 70 on shuttle 60 each have a guide blade 82 and 84, respectively, mounted thereon. Blades 82 and 84 diverge outwardly as they project forwardly from the arms 68 and 70, to thereby shift a specimen carrier 18 transversely into alignment between the arms 68 and 70. Blades 82 and 84 are preferably formed of a resilient and flexible material so that shuttle 60 can shift fully against the outside guide rails 28 (see FIG. 2) to release a carrier 18 onto either conveyor 12 or 14.

A presence sensor 86 is positioned adjacent each outward extent of shuttle 60 to detect the presence of a carrier 18 within shuttle 60 on either conveyor 12 or 14. An exit sensor 88 is positioned downstream of shuttle 60 along each conveyor 12 and 14, to detect the presence of a carrier that has exited the shuttle along either conveyor.

A pair of carrier stop arms 90 and 92 project transversely outwardly from back 56 and extend partially over conveyors 12 and 14, respectively. However, stop arms 90 and 92 do not project far enough to prevent a carrier 18 from passing between the stop arm and the associated outside guide rail 28, if aligned with the opening therebetween by carrier shuttle 60.

Referring once again to FIG. 2, the operation of transfer apparatus 10 is as follows. While specimen carriers 18 travel along both conveyors 12 and 14 during operation the description of the operation of the transfer apparatus will assume that a carrier 18 first reaches queue 20 along conveyor 12. The rest position of all four shafts 36, 38, 44 and 46 of queue 20 are in an extended position, so that a carrier 18 is prevented from advancing beyond the associated shaft until the particular shaft is retracted. Thus, carrier 18, on conveyor 12 will first contact extended shaft 36 and stop in position "A". Sensor 40 detects the presence of carrier 18, and retracts shaft 36 to permit the carrier to proceed downstream. Carrier 18 is then stopped by extended shaft 38. When rearward sensor 42 detects the presence of carrier 18 at position "B", a barcode scanner 94 is turned on to scan the barcode label on the side of carrier 18. This data is then transmitted to the command module 24, which will determine the appropriate action to take, based upon priority rules and guidelines set up by the LAS.

Figure 6:
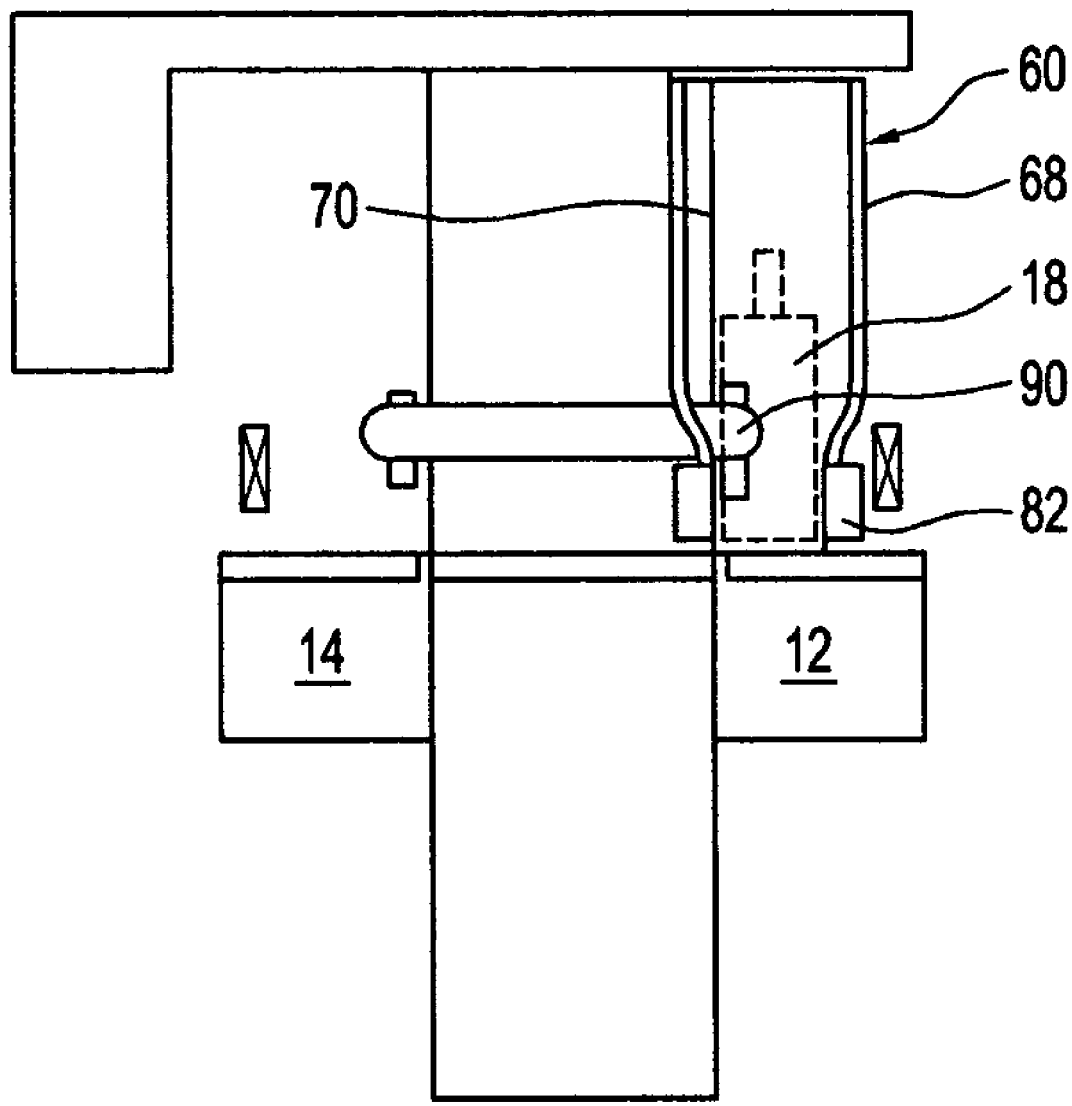
FIG. 6 is a front elevational view of the transfer apparatus showing the shuttle in a first position.
Figure 7:
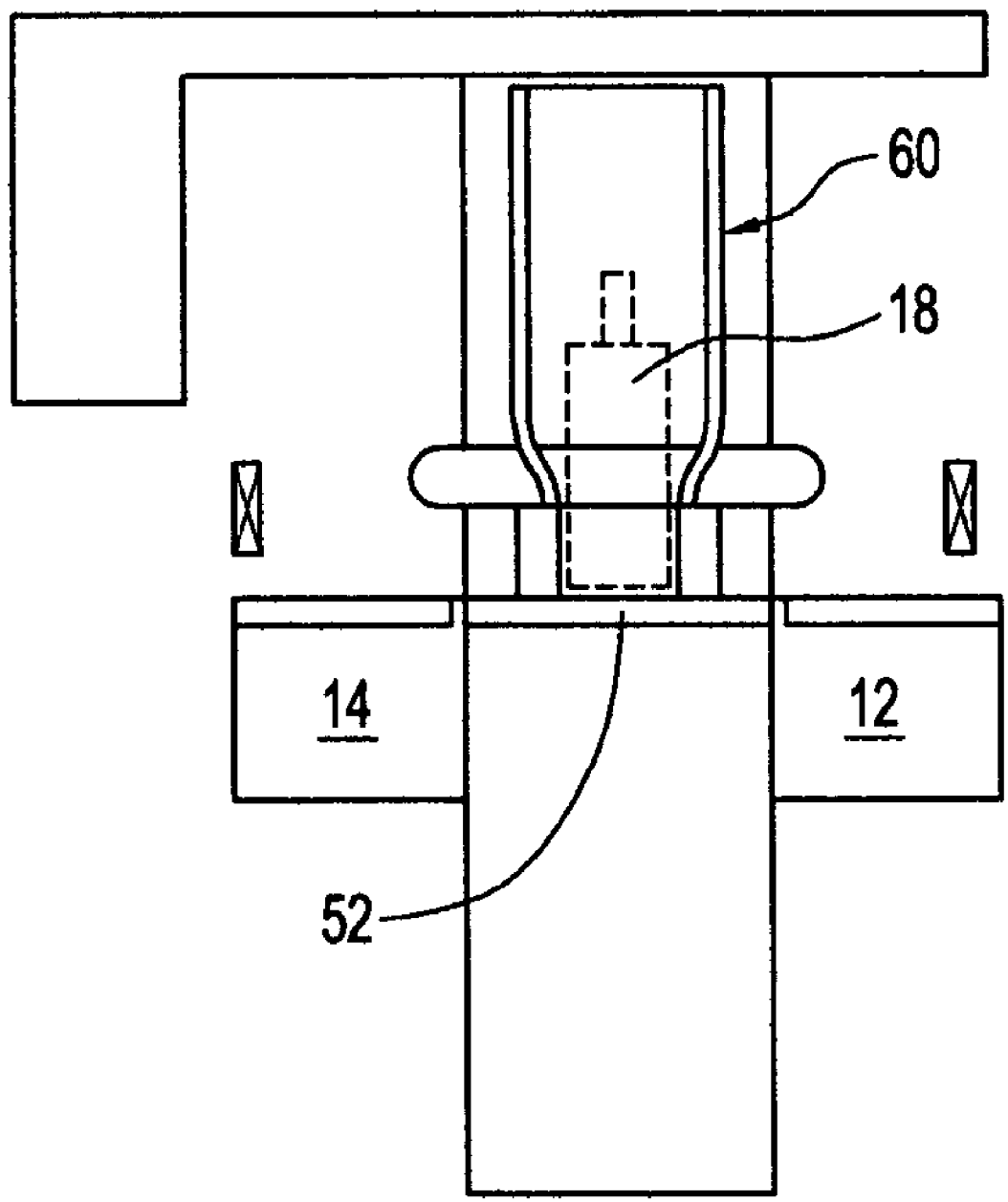
FIG. 7 is a front elevational view of the transfer apparatus showing the shuttle in a second position.
Figure 8:
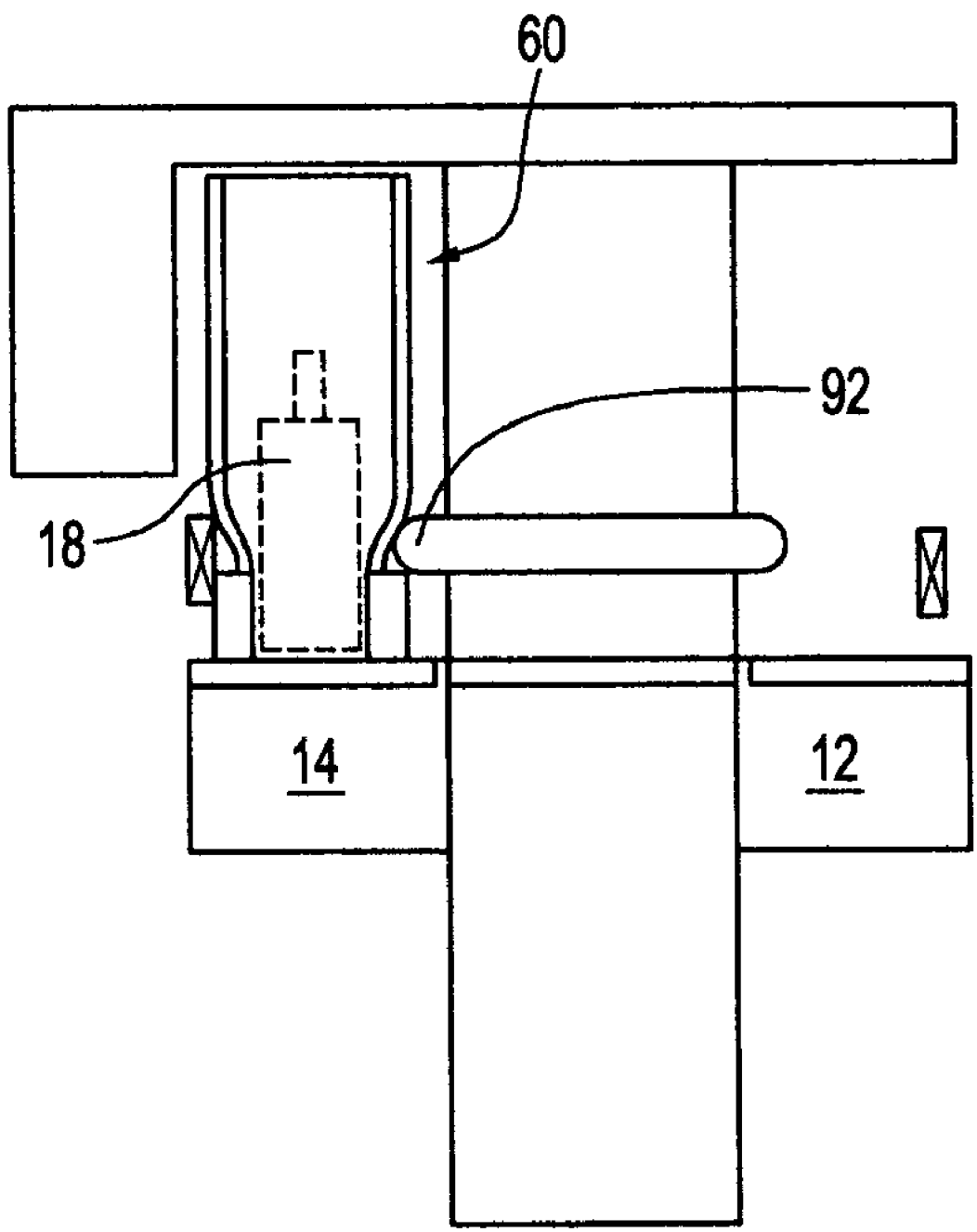
FIG. 8 is a front elevational view of the transfer apparatus showing the shuttle in a third position.

Once the command module has determined the action to be taken, shaft 42 is retracted, and carrier 18 proceeds to a "hold" position "C" on conveyor 12. As shown in FIG. 6, the "hold" position locates shuttle 60 slightly inwardly from the lane of conveyor 12, so that blade 82 directs the carrier between arms 68 and 70, and into contact with stop 90. If carrier 18 is to be diverted to conveyor 14, then command module 24 will instruct lane changer 22 to move shuttle 60 across platform 52, as shown in FIG. 7, to the "release" position "D" on conveyor 14. The release position "D" locates carrier 18 on conveyor 14 so that it bypasses stop 92, to permit the carrier to proceed downstream, as shown in FIG. 8. As the carrier leaves lane changer 22 it will pass exit sensor 88 at position "E", which will confirm that the desired action has occurred.

In the alternative, if carrier 18 is to be released along conveyor 12 rather than diverted to conveyor 14, then shuttle 60 will be instructed to move outwardly from the "hold" position to the "release" position. This movement will cause carrier 18 to be moved outwardly beyond the end of stop 90, permitting the carrier to proceed downstream on conveyor 12. As the carrier leaves lane changer 22, it will pass exit sensor 88 at position "F", which will confirm that the desired action has been taken.

This same sequence of actions occurs with a carrier 18 that approaches queue 20 along conveyor 14, with the same options of releasing the carrier on the same conveyor, or diverting the carrier to conveyor 12.

Whereas the invention has been shown and described in connection with the preferred embodiment thereof, many modifications, substitutions and additions may be made which are within the intended broad scope of the appended claims.

What is claimed is:

1. A transfer apparatus for shifting specimen carriers between two conveyors of a dual conveyor track, the track of the type having first and second parallel, spaced apart conveyors with upper surfaces within a single plane, the conveyors operable in the same longitudinal direction, the transfer apparatus comprising:
   a frame connected to the track for supporting an operable shuttle;
   a shuttle operably connected to the frame to move transversely between the conveyors and generally perpendicular to the movement of specimen carriers on the conveyors;
   a first stop member on said frame, projecting partially over the first conveyor;
   a second stop member on said frame, projecting partially over the second conveyor;
   said shuttle having a pair of parallel arms spaced apart a distance to receive a specimen carrier therebetween;
   said shuttle operable to a first "hold" position with the shuttle arms located such that a specimen carrier therebetween is in contact with the first stop member, to thereby prevent downstream movement of a carrier on the first conveyor;
   said shuttle operable to a first "release" position with the shuttle arms located such that a specimen carrier therebetween bypasses the first stop member and is moved downstream through the shuttle arms on the first conveyor;
   said shuttle operable to a second "release" position with the shuttle arms located such that a specimen carrier therebetween bypasses the second stop member and is moved downstream through the shuttle arms on the second conveyor;
   said shuttle also being operable to a second "hold" position with the shuttle arms located such that a specimen carrier therebetween is in contact with the second stop member to thereby prevent downstream movement of a carrier on the second conveyor;
   a drive assembly on the frame for selectively moving the shuttle among the first "hold" position, the second "hold" position, the first "release" position and the second "release" position; and
   an electronic command module with a processor therein, said command module electrically connected to the motor and said processor programmed to selectively drive the motor to move the shuttle to a predetermined position.

2. The transfer apparatus of claim 1, wherein said frame further includes a first sensor located to detect the presence of a carrier within the arms of the shuttle in the first "hold" position, said sensor electronically connected to the command module for transmitting detection information thereto.

3. The transfer apparatus of claim 2, wherein said frame further includes a second sensor located to detect the presence of a carrier within the arms of the shuttle in the second "hold" position, said sensor electronically connected to the command module for transmitting detection information thereto.

4. A transfer apparatus for shifting specimen carriers between two conveyors of a dual conveyor track, the track of the type having first and second parallel, spaced apart conveyors with upper surfaces within a single plane, the conveyors operable in the same longitudinal direction, the transfer apparatus comprising:
   a frame connected to the track for supporting an operable shuttle;

a shuttle operably connected to the frame to move transversely between the conveyors and generally perpendicular to the movement of specimen carriers on the conveyors;

a first stop member on said frame, projecting partially over the first conveyor;

a second stop member on said frame, projecting partially over the second conveyor;

said shuttle having a pair of parallel arms spaced apart a distance to receive a specimen carrier therebetween;

said shuttle operable to a first "hold" position with the shuttle arms located such that a specimen carrier therebetween is in contact with the first stop member, to thereby prevent downstream movement of a carrier on the first conveyor;

said shuttle operable to a first "release" position with the shuttle arms located such that a specimen carrier therebetween bypasses the first stop member and is moved downstream through the shuttle arms on the first conveyor;

said shuttle operable to a second "release" position with the shuttle arms located such that a specimen carrier therebetween bypasses the second stop member and is moved downstream through the shuttle arms on the second conveyor;

said shuttle also being operable to a second "hold" position with the shuttle arms located such that a specimen carrier therebetween is in contact with the second stop member to thereby prevent downstream movement of a carrier on the second conveyor;

a drive assembly on the frame for selectively moving the shuttle among the first "hold" position, the second "hold" position, the first "release" position and the second "release" position;

said frame further including a support plate mounted on the upper end thereof supporting said shuttle and said drive assembly; and said shuttle arms being suspended from a slide, said slide being slidably mounted along a linear rail, and said motor being connected to the slide to selectively move the slide along the rail.

5. The transfer apparatus of claim 4, wherein said motor is suspended from the support plate on the frame.

6. The transfer apparatus of claim 3, wherein said frame further includes a first exit sensor located downstream of the first sensor along the first conveyor, to detect the presence of a carrier that has exited the arms of the shuttle in the first "release" position, said sensor electronically connected to the command module for transmitting detection information thereto.

7. The transfer apparatus of claim 6, wherein said frame further includes a second exit sensor located downstream of the second sensor along the second conveyor, to detect the presence of a carrier that has exited the arms of the shuttle in the second "release" position, said sensor electronically connected to the command module for transmitting detection information thereto.

8. A transfer apparatus for shifting specimen carriers between two conveyors of a dual conveyor track, the track of the type having first and second parallel, spaced apart conveyors with upper surfaces within a single plane, the conveyors operable in the same longitudinal direction, the transfer apparatus comprising:

a frame connected to the track for supporting an operable shuttle;

a shuttle operably connected to the frame to move transversely between the conveyors and generally perpendicular to the movement of specimen carriers on the conveyors;

a first stop member on said frame, projecting partially over the first conveyor;

a second stop member on said frame, projecting partially over the second conveyor;

said shuttle having a pair of parallel arms spaced apart a distance to receive a specimen carrier therebetween;

said shuttle operable to a first "hold" position with the shuttle arms located such that a specimen carrier therebetween is in contact with the first stop member, to thereby prevent downstream movement of a carrier on the first conveyor;

said shuttle operable to a first "release" position with the shuttle arms located such that a specimen carrier therebetween bypasses the first stop member and is moved downstream through the shuttle arms on the first conveyor;

said shuttle operable to a second "release" position with the shuttle arms located such that a specimen carrier therebetween bypasses the second stop member and is moved downstream through the shuttle arms on the second conveyor;

said shuttle also being operable to a second "hold" position with the shuttle arms located such that a specimen carrier therebetween is in contact with the second stop member to thereby prevent downstream movement of a carrier on the second conveyor;

a drive assembly on the frame for selectively moving the shuttle among the first "hold" position, the second "hold" position, the first "release" position and the second "release" position; and a queue positioned upstream of said shuttle between said conveyors, for selectively restraining specimen carriers on the conveyors upstream of the shuttle and selectively releasing a specimen carrier from one of said conveyors in response to instructions from the command module, said queue electronically connected to the command module to receive instructions therefrom.

9. The transfer apparatus of claim 8, wherein said queue includes:

a housing mounted between the conveyors;

a first retractable shaft projecting from a downstream end of the housing and over the first conveyor, to restrain a specimen carrier from movement along the first conveyor when extended;

a motor in said housing connected to said first shaft for selectively extending and retracting said shaft, said motor electrically connected to the command module and responsive to instructions from the command module;

a second retractable shaft projecting from a downstream end of the housing and over the second conveyor, to restrain a specimen carrier from movement along the second conveyor when extended;

said motor connected to said second shaft for selectively extending and retracting said shaft;

a first sensor adjacent said first shaft for detecting the presence of a specimen carrier restrained by the first shaft;

said first sensor electrically connected to the command module and adapted to transmit detection data to the command module; and a second sensor adjacent said second shaft for detecting the presence of a specimen carrier restrained by the second shaft;

said second sensor electrically connected to the command module and adapted to transmit detection data to the command module.

10. The transfer apparatus of claim 9, wherein said queue first and second shafts are connected together, such that the retraction of one shaft causes the extension of the other, whereby no more than one specimen carrier may be released at a time by the queue.

11. The transfer apparatus of claim 9, wherein said queue further includes:

a first scanner adjacent said first shaft for scanning a specimen carrier restrained by the first shaft, to collect identification data therefrom;

said first scanner electrically connected to the command module and adapted to transmit identification data to the command module; and a second scanner adjacent said second shaft for scanning a specimen carrier restrained by the second shaft, to collect identification data therefrom;

said second scanner electrically connected to the command module and adapted to transmit identification data to the command module.

12. The transfer apparatus of claim 11, wherein said first scanner is activated to scan in response to the detection of the presence of a specimen carrier by the first sensor, and wherein the second scanner is activated to scan in response to the detection of the presence of a specimen carrier by the second sensor.

13. The transfer apparatus of claim 12, wherein said queue further includes:

a third retractable shaft projecting from an upstream end of the housing and over the first conveyor, to restrain a specimen carrier from movement along the first conveyor when extended;

a second motor in said housing connected to said third shaft for selectively extending and retracting said shaft, said motor electrically connected to the command module and responsive to instructions from the command module;

a fourth retractable shaft projecting from an upstream end of the housing and over the second conveyor, to restrain a specimen carrier from movement along the second conveyor when extended;

said second motor connected to said fourth shaft for selectively extending and retracting said shaft;

a third sensor adjacent said third shaft for detecting the presence of a specimen carrier restrained by the third shaft;

said third sensor electrically connected to the command module and adapted to transmit detection data to the command module; and a fourth sensor adjacent said fourth shaft for detecting the presence of a specimen carrier restrained by the fourth shaft;

said fourth sensor electrically connected to the command module and adapted to transmit detection data to the command module.

* * * * *